United States Patent
Dumot

(10) Patent No.: US 11,344,317 B2
(45) Date of Patent: May 31, 2022

(54) ENDOSCOPIC CLOSURE DEVICE

(71) Applicant: University Hospitals Cleveland Medical Center, Cleveland, OH (US)

(72) Inventor: John A. Dumot, Chagrin Falls, OH (US)

(73) Assignee: University Hospitals Cleveland Medical Center, Cleveland, OH (US)

( * ) Notice: Subject to any disclaimer, the term of this patent is extended or adjusted under 35 U.S.C. 154(b) by 154 days.

(21) Appl. No.: 16/650,634

(22) PCT Filed: Oct. 5, 2018

(86) PCT No.: PCT/US2018/054655
§ 371 (c)(1),
(2) Date: Mar. 25, 2020

(87) PCT Pub. No.: WO2019/071158
PCT Pub. Date: Apr. 11, 2019

(65) Prior Publication Data
US 2020/0222054 A1    Jul. 16, 2020

Related U.S. Application Data

(60) Provisional application No. 62/568,459, filed on Oct. 5, 2017.

(51) Int. Cl.
*A61B 17/128* (2006.01)
*A61B 17/122* (2006.01)
*A61B 17/00* (2006.01)

(52) U.S. Cl.
CPC ........ *A61B 17/1285* (2013.01); *A61B 17/122* (2013.01); *A61B 2017/0034* (2013.01); *A61B 2017/00349* (2013.01)

(58) Field of Classification Search
CPC ..... A61B 17/08; A61B 17/083; A61B 17/122; A61B 17/128; A61B 17/1285; A61B 2017/088
See application file for complete search history.

(56) References Cited

U.S. PATENT DOCUMENTS 5,817,111 A * 10/1998 Riza ................. A61B 17/06109
606/148
6,267,761 B1 * 7/2001 Ryan ................. A61B 18/1442
606/32

(Continued)

OTHER PUBLICATIONS

European Search Report from related European Application No. 18865001.4 dated May 11, 2021.

(Continued)

*Primary Examiner* — Ryan J. Severson
(74) *Attorney, Agent, or Firm* — Fay Sharpe LLP

(57) ABSTRACT

Surgical closure devices, surgical systems, and methods of endoscopically closing tissue tears are disclosed. The surgical closure device includes a housing and a grasping member. The grasping member is configured for movement relative to the housing. The surgical systems include such a surgical closure device and an endoscope including an insertion tube and a cable. The methods of endoscopically closing a tear in a tissue include passing such a surgical closure device through an endoscope to the tear, engaging a portion of tissue on one side of the tear using the grasping member, positioning the receiving section of the housing on another side of the tear, and moving the grasping member toward the receiving section of the housing and position the grasping member and the receiving portion of the housing in a relatively closed relationship, thereby closing the tear in the tissue.

17 Claims, 20 Drawing Sheets

(56) References Cited

U.S. PATENT DOCUMENTS

| | | | | |
|---|---|---|---|---|
| 8,066,718 B2* | 11/2011 | Weisel | ............... | A61B 17/0469 |
| | | | | 606/139 |
| 8,556,916 B2* | 10/2013 | Torrie | ................ | A61B 17/0482 |
| | | | | 606/148 |
| 8,585,714 B2* | 11/2013 | Weisel | ............... | A61B 17/0485 |
| | | | | 606/139 |
| 8,591,529 B2 | 11/2013 | Smith | | |
| 9,693,759 B2* | 7/2017 | Seguy | ...................... | A61B 1/05 |
| 9,861,379 B2* | 1/2018 | Chin | ..................... | A61B 17/08 |
| 9,867,624 B2* | 1/2018 | Satake | ............... | A61B 17/1285 |
| 9,931,114 B2* | 4/2018 | Stewart | .............. | A61B 17/0485 |
| 10,071,231 B2* | 9/2018 | Yokota | ............ | A61M 25/09041 |
| 10,368,871 B2* | 8/2019 | Dumot | ................... | A61B 17/10 |
| 11,000,300 B2* | 5/2021 | Verma | ............... | A61B 17/32056 |
| 2006/0069399 A1* | 3/2006 | Weisel | ............... | A61B 17/0469 |
| | | | | 606/148 |
| 2007/0038229 A1* | 2/2007 | de la Torre | ......... | A61B 17/0483 |
| | | | | 606/139 |
| 2012/0209300 A1* | 8/2012 | Torrie | ................ | A61B 17/0469 |
| | | | | 606/148 |
| 2014/0243890 A1 | 8/2014 | Dumot | | |
| 2014/0336532 A1 | 11/2014 | Seguy | | |
| 2015/0238194 A1 | 8/2015 | Hingston et al. | | |
| 2016/0015405 A1 | 1/2016 | Chin et al. | | |
| 2017/0215884 A1 | 8/2017 | Satake et al. | | |
| 2017/0232237 A1 | 8/2017 | Yokota et al. | | |
| 2019/0357905 A1* | 11/2019 | Dumot | ............. | A61B 17/00234 |
| 2020/0222054 A1* | 7/2020 | Dumot | ................ | A61B 17/122 |

OTHER PUBLICATIONS

International Search Report dated Dec. 20, 2018 from PCT/US2018/054655.

* cited by examiner

ENDOSCOPIC CLOSURE DEVICE

CROSS-REFERENCE TO RELATED APPLICATIONS

This application is a 371 of PCT Patent Application Serial No. PCT/US2018/054655, filed Oct. 5, 2018, which claims priority to U.S. Provisional Patent Application Ser. No. 62/568,459, filed Oct. 5, 2017, the entirety of which is fully incorporated by reference herein.

BACKGROUND

The present disclosure relates to surgical closure devices for endoscopically closing a tear in a tissue. In particular, the present disclosure relates to endoscopic closure devices that are adapted to be delivered by an associated endoscope with a grasping member configured for movement relative to a housing.

Less invasive surgical procedures can reduce patient trauma, and as a result, may reduce the length of hospital stays, as well as hospital and medical costs. Endoscopic surgery provides a significant opportunity to reduce the invasiveness of numerous surgical procedures. This type of surgery involves the use of an endoscope, an instrument that permits the visual inspection and magnification of cavities within the body. Endoscopes may be flexible, semi-flexible or rigid. An endoscope may be inserted through a small surgical incision to view organ structures in a body cavity or through a natural orifice to view lumen-containing organs in the gastrointestinal, respiratory, genital and urinary tracts. Endoscopes typically have channels for irrigation, suction, and the insertion of accessory instruments when a surgical procedure is performed.

During a surgical procedure, surgeons often are required to repair or reconstruct a tear or defect or otherwise approximate or fixate tissue or other material by suturing. The ability to suture through an endoscope technically is limited. In response to this problem, surgeons have sought alternatives to conventional suturing techniques that are more appropriate for use through an endoscope. Among these alternatives is the use of endoscopic clips for closing a tear in tissue.

BRIEF DESCRIPTION

The present disclosure relates to a surgical closure device for endoscopically closing a tear in a tissue. In particular, the present disclosure relates to an endoscopic closure device adapted to be delivered by an associated endoscope with a grasping member configured for movement relative to a housing.

Disclosed in various embodiments herein are surgical closure devices, comprising: a housing comprising a longitudinal axis, a first end, a second end opposite the first end, a slot at the second end of the housing, and a receiving portion at the second end of the housing and spaced apart from the slot; and a grasping member comprising a proximal end, a distal end opposite the proximal end, and a tine at the distal end of the grasping member, the grasping member passing through the slot in the housing and configured for movement relative to the housing such that the tine can engage the receiving portion of the housing.

In certain constructions, the grasping member is configured for bi-directional movement toward the housing and away from the housing along a direction parallel to the longitudinal axis of the housing.

The receiving portion of the housing and the tine of the grasping member can be complementarily shaped.

The proximal end of the grasping member can be configured for movement within the housing and the distal end of the grasping member can be configured for movement outside of the housing. The grasping member can further comprise a main body portion that passes through the slot in the housing. The main body portion of the grasping member can have a first side edge and a second side edge opposite the first side edge. In certain embodiments, at least one of the first and second side edges has a plurality of protrusions extending outwardly therefrom. In particular embodiments, each of the first and second side edges has a plurality of protrusions extending outwardly therefrom. In such embodiments, every protrusion extending outwardly from the first side edge can correspond to a respective protrusion extending outwardly from the second side edge to define a pair of corresponding protrusions that are positioned in a same latitudinal level and parallel to one another. In alternative such embodiments, every protrusion extending outwardly from the first side edge can be at a different latitudinal level than every protrusion extending outwardly from the second side edge. In particular embodiments, each of the plurality of protrusions includes a base portion and an angled portion, the base portion extending outwardly from the first side edge substantially perpendicular thereto, and the angled portion extending outwardly from the first side edge and meeting the base portion at a point spaced apart from the first side edge, with the angled portion being closer to the proximal end of the grasping member than the distal end of the grasping member.

In certain constructions, the tine of the grasping member is located on an end portion of the grasping member, the end portion protruding outwardly from the main body portion of the grasping member. In further embodiments, the end portion protrudes outwardly from the main body portion of the grasping member and extends back toward the main body portion so as to form a hook. The grasping member can include a base portion that is spaced a fixed distance apart from the tine.

The proximal end of the grasping member can, in certain embodiments, comprise a base that engages the main body portion, the base being wider than the slot in the housing; and a lip extending away from the main body portion.

The grasping member can be closable along the direction substantially parallel to the axis of the housing through uni-directional movement into the housing. The grasping member can be movable toward the receiving portion of the housing to close and position the grasping member and the receiving portion of the housing in a relatively closed relationship. The grasping member can be movable away the receiving portion of the housing to open and position the grasping member and the receiving portion of the housing in a relatively open relationship.

In particular embodiments, the main body portion of the grasping member includes a first side edge and a second side edge opposite the first side edge, each of the first and second side edges having a plurality of protrusions extending outwardly therefrom; and the protrusions engage the housing to retain the tine of the grasping member in a fixed relationship relative to the receiving portion of the housing.

Also disclosed in various embodiments herein is a surgical system, comprising: an endoscope including an insertion tube having a cable disposed therein; and a surgical closure device adapted to be delivered by the endoscope, the surgical closure device including a housing comprising a longitudinal axis, a first end, a second end opposite the first end, a slot at the second end of the housing, and a receiving portion at the second end of the housing and spaced apart from the slot; and a grasping member comprising a proximal end, a distal end opposite the proximal end, and a tine at the distal end of the grasping member, the grasping member passing through the slot in the housing and configured for movement relative to the housing; wherein the insertion tube of the endoscope is cooperatively engaged with the first end of the housing; and wherein the cable of the endoscope is cooperatively engaged with and adapted to move the grasping member relative to the housing such that the tine can engage the receiving portion of the housing.

An end of the cable can be shaped complementary to a proximal end of the grasping member such that the proximal end of the grasping member cooperatively engages with the end of the cable. In certain constructions, the endoscope further comprises a first handle and a second handle, wherein the first handle is adapted for movement relative to the second handle and cooperatively engages with the cable, and wherein the second handle engages the insertion tube, such that the first handle is adapted to move the grasping member relative to the housing of the surgical closure device.

Further disclosed in various embodiments herein are methods of endoscopically closing a tear in a tissue, the methods comprising: passing a surgical closure device through an endoscope to the tear, the surgical closure device including a housing comprising a longitudinal axis, a first end, a second end opposite the first end, a slot at the second end of the housing, and a receiving portion at the second end of the housing and spaced apart from the slot; and a grasping member comprising a proximal end, a distal end opposite the proximal end, and a tine at the distal end of the grasping member, the grasping member passing through the slot in the housing and configured for movement relative to the housing; engaging a portion of tissue on one side of the tear using the grasping member; positioning the receiving section of the housing on another side of the tear; and moving the grasping member toward the receiving section of the housing and position the grasping member and the receiving portion of the housing in a relatively closed relationship, thereby closing the tear in the tissue.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
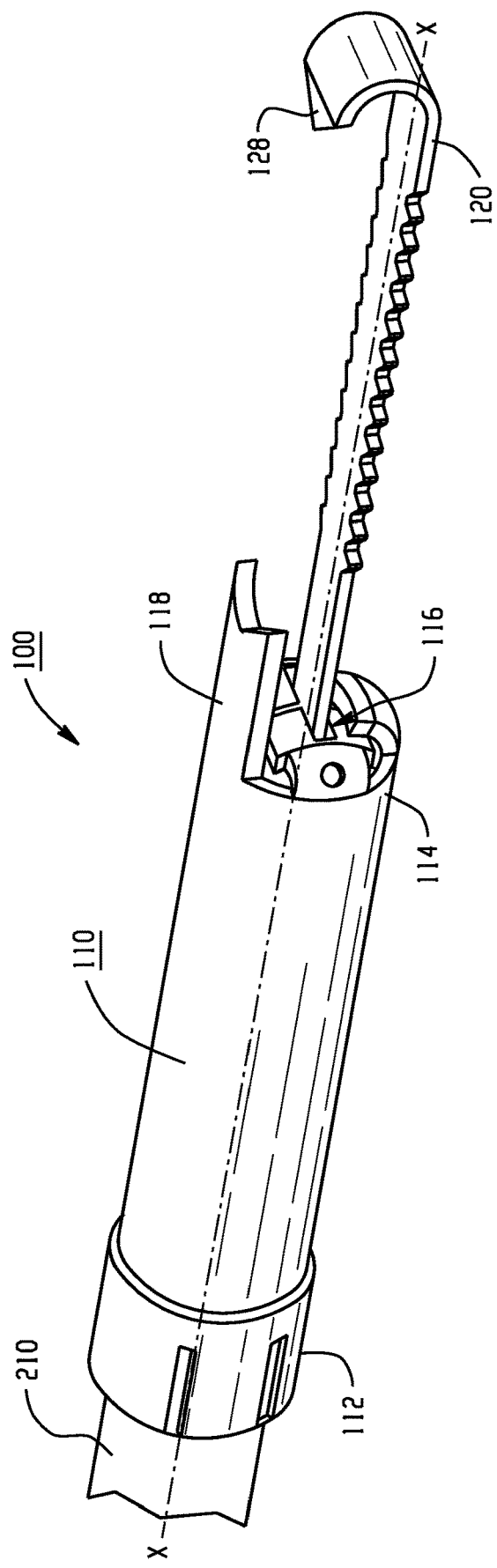
FIG. 1 is a perspective view of a portion of a surgical system including a first exemplary embodiment of a surgical closure device according to the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g. "about 2 to about 4" also discloses the range "from 2 to 4." Generally, the terms "about" and "approximately" may refer to plus or minus 10% of the indicated number.

Surgeons have sought alternatives to conventional suturing techniques that are more appropriate for use through an endoscope. Tissue closure devices typically include ligation loops or endoscopic clips in which the tissue-closing motion is in a direction that is approximately perpendicular to the axis of the endoscope accessory channel. Tissue closure along this direction has some limitations and difficulties with respect to positioning the closure device, as well as being able to span the width of a larger tear or defect. Typically, these devices also have fixed relationships that limit the surgeon's ability to position the clip appropriately in relation to a particular tear or defect or other area in need of treatment.

The present disclosure recognizes shortcomings with conventional surgical closure devices and provides an improved surgical closure device that is configured to align and deploy along an endoscope accessory channel.

FIG. 1 is a perspective view of a first exemplary embodiment of such an improved surgical closure device according to the present disclosure in use in a surgical system. This surgical closure device 100 of this exemplary embodiment includes a housing 110 and a grasping member 120. As will be appreciated, the surgical closure devices of the present disclosure are adapted to be delivered by an associated endoscope (e.g., through an endoscope accessory channel).

As seen in FIG. 1, the grasping member 120 is configured for bi-directional movement toward and away from the housing 110 along a direction parallel to a longitudinal axis X-X of the housing 110. In particular, the grasping member 120 is configured for bi-directional movement into and out of the housing 110. In this exemplary embodiment, the housing 110 is cylindrical and is defined by a sidewall extending between a first end 112 of the housing 110 and a second end 114 of the housing 110. The cylindrical housing 110 has a hollow interior within which the grasping member 120 moves. In this exemplary embodiment, the grasping member 120 passes into the hollow interior of the housing 110 through a slot 116 in the housing. The housing 110 is configured for attachment to the associated endoscope (e.g., to an insertion tube 210 of the associated endoscope) at the first end 112 of the housing 110, while the slot 116 in the housing 110 is located at the opposite second end 114 thereof. That is, the first end 112 of the housing 110 and the second end 114 of the housing 110 define opposing ends of the housing 110. With continued reference to FIG. 1, it can be seen that the housing 110 includes a receiving section 118 at the second end 114 of the housing. In particular, the receiving section 118 shown here extends outwardly away from the second end 114 of the housing along a direction substantially parallel to the axis X-X of the housing 110. The receiving section 118 of the housing 110 is spaced apart from the slot 116 in the housing 110. Put another way, the receiving section 118 is located a fixed distance from the slot 116, and the receiving section 118 and the slot 116 do not move relative to one another. The receiving section 118 of the housing is aligned with a tine 128 of the grasping member.

Figure 2:
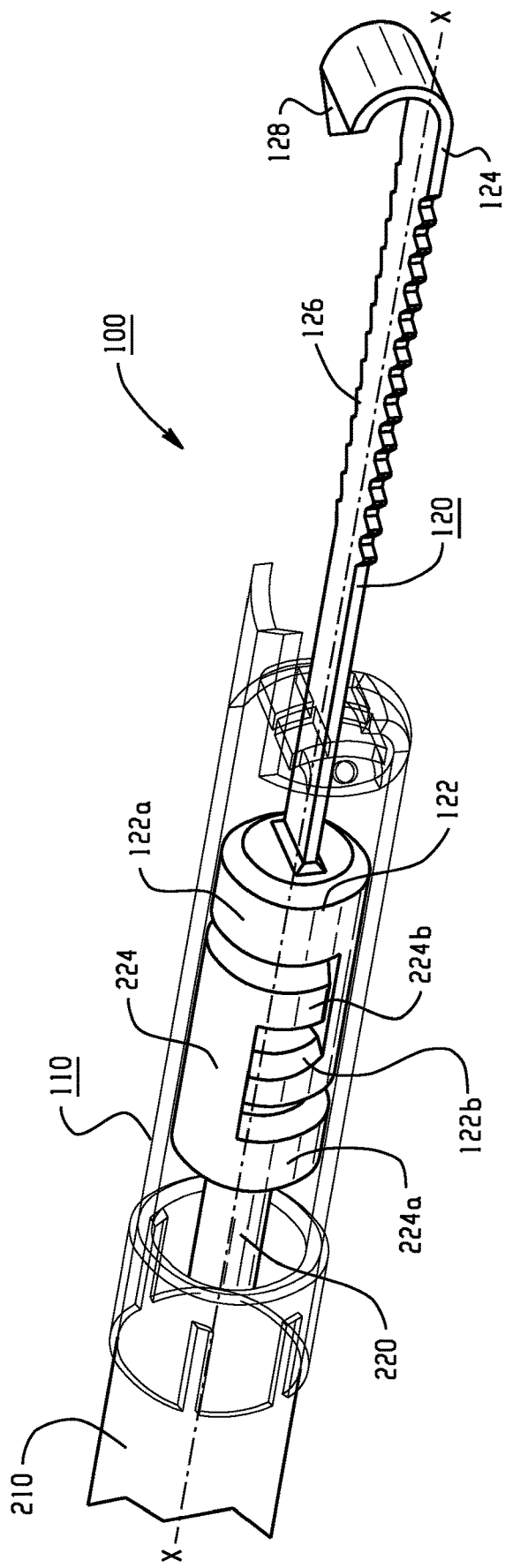
FIG. 2 is another perspective view of the portion of the surgical system and surgical closure device of FIG. 1, with a transparent housing to show additional features thereof.

FIG. 2 is another perspective view of surgical closure device 100. Here, only the outline of the housing 110 is depicted, so as to more clearly illustrate certain principles of the surgical closure device 100. As previously explained, the grasping member 120 is movable toward the housing 110. In particular, as shown in FIG. 1 and FIG. 2, the grasping member 120 can be moved away from the housing 110 so as to position the grasping member 120 and the housing 110 in a relatively open relationship.

In this exemplary embodiment, the grasping member 120 includes a main body portion 126 extending between a proximal end 122 and a distal end 124 of the grasping member 120. As seen, the proximal end 122 of the grasping member 120 and the distal end 124 of the grasping member 120 define opposing ends of the grasping member 120. The proximal end 122 of the grasping member 120 is located within the housing 110 and cannot pass through the slot 116. That is, the slot 116 in the housing 110 is sized so as to be smaller than the proximal end 122 of the grasping member 120. In this way, when in use, the proximal end 122 of the grasping member 120 cannot extend past the second end 114 of the housing 110, but may extend to or past the first end 112 of the housing 110 depending upon the relative lengths of the grasping member 120 and the housing 110.

On the other hand, the distal end 124 of the grasping member 120 is configured for movement outside of the housing 110. That is, the slot 116 in the housing 110 is typically also sized so as to be smaller than the distal end 124 of the grasping member 120, so the distal end 124 of the grasping member 120 cannot pass through the slot 116. The main body portion 126 of the grasping member 120 passes through the slot 116 at the second end 114 thereof of the housing 110 and moves both into and out of the housing 110 through the slot 116. The grasping member 120 includes a tine 128 at the distal end 124 thereof. The tine 128 of the grasping member 120 moves relative to the housing 110 along a direction substantially parallel to the axis X-X of the housing 110, but cannot enter the hollow interior of the housing 110. In this way, the tine 128 can engage the receiving portion 118 of the housing 110.

With continued reference to FIG. 2, it can be seen that the proximal end 122 of the grasping member 120 has a U-shaped cross-section when viewed from the side. The proximal end 122 of the grasping member 120 is defined by a base 122*a* and a lip 122*b* which together form a U-shaped channel. Similarly, an end 224 of a cable 220 of the associated endoscope also has a U-shaped cross-section defined by a base 224*a*, a lip 224*b*, and a hollow channel (not labeled) therebetween.

The lip 122*b* at the proximal end 122 of the grasping member 120 extends into the channel at the end 224 of cable 220, and the lip 224*b* at the end 224 of cable 220 extends into the channel 122*c* at the proximal end 122 of grasping member 120. Put more generally, the proximal end 122 of the grasping member 120 and the end 224 of the cable 220 are shaped complementarily to one another to engage each other during movement along longitudinal axis X-X, and to be disengaged by movement in the radial direction (i.e. normal to the longitudinal axis). The proximal end 122 of the grasping member 120 and the end 224 of the cable 220 are thus removably coupled to one another. The cable is adapted to move the grasping member 120 relative to the housing 110 (i.e., into and out of the housing 110) along the direction substantially parallel to the axis X-X of the housing 110. In particular constructions, the end 224 of the cable 220 is sized so as to fit into the hollow interior of the housing 110.

The cable 220 is disposed within an insertion tube 210, with the cable 220 being movable within the insertion tube 210 along a direction substantially parallel to the axis X-X of the housing 110. Again, the insertion tube 210 is cooperatively engaged with the housing 110. In this way, the insertion tube 210 and housing 110 help to protect both the cable 220 and the grasping member 220 from unwanted contact or material, which is especially desirably when the surgical closure device or surgical systems of the present disclosure are to be used inside a body.

Figure 3:
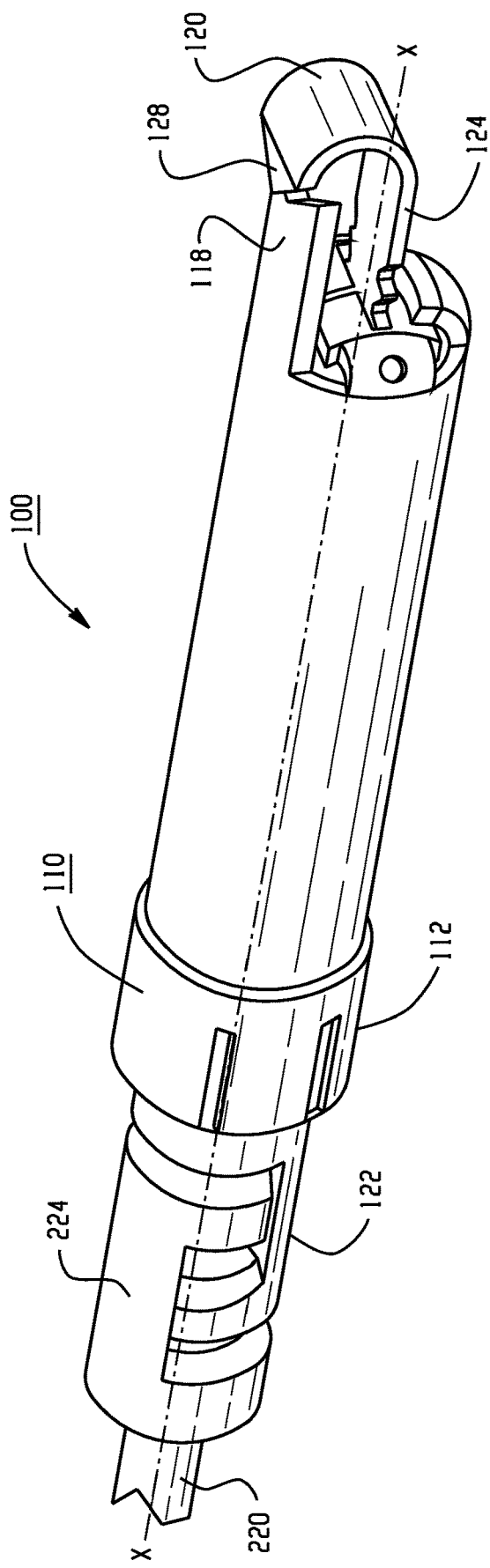
FIG. 3 is another perspective view of the portion of surgical system and surgical closure device of FIG. 1, with the insertion tube of the surgical system removed to show additional features thereof.
Figure 4:
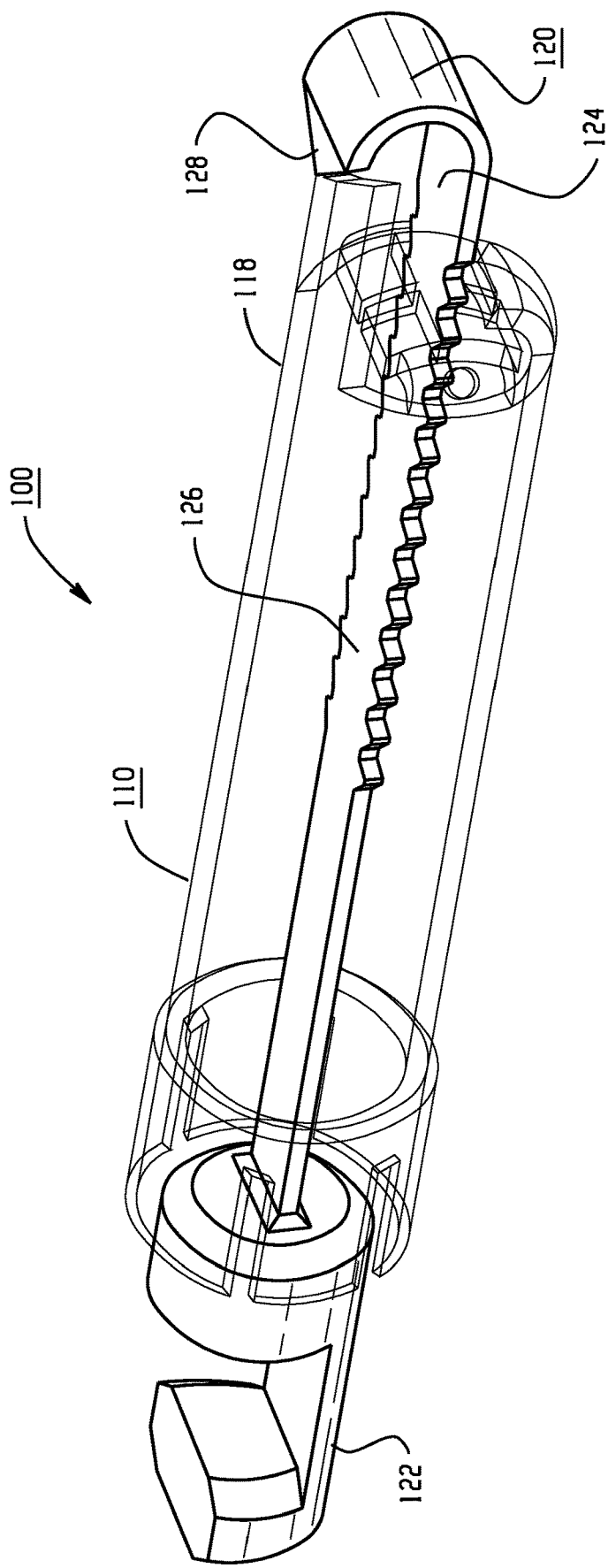
FIG. 4 is a perspective view of the surgical closure device of FIG. 1, with a transparent housing to show additional features thereof.

FIG. 1 and FIG. 2 show the grasping member 120 in an open position relative to the housing 110. FIG. 3 and FIG. 4 show the grasping member 120 and the housing 110 of the device 100 in a closed position relative to the housing 110. The terms "open" and "closed" are used here relative to each other as well. In FIG. 3, the insertion tube of the associated endoscope is removed so as to more clearly illustrate certain principles of the surgical closure device 100. In FIG. 4, only the outline of the housing 110 is depicted, so as to more clearly illustrate certain additional principles of the surgical closure device 100.

Referring first to FIG. 3, it can be seen that in the closed position, the tine 128 of the grasping member 120 engages the receiving section 118 of the housing 110. The distal end 124 of the grasping member is much closer to the housing 110. The proximal end 122 of the grasping member is now located outside of the housing, beyond the first end 112. The cable 220 and its end 224 are now visible, still engaging the proximal end 122.

Next, FIG. 4 shows the majority of the main body portion 126 located within the housing 110. The proximal end 122 extends past the housing, and the distal end 124 of the grasping member 120 includes the tine 128, which is engaging the receiving section 118.

Figure 5:
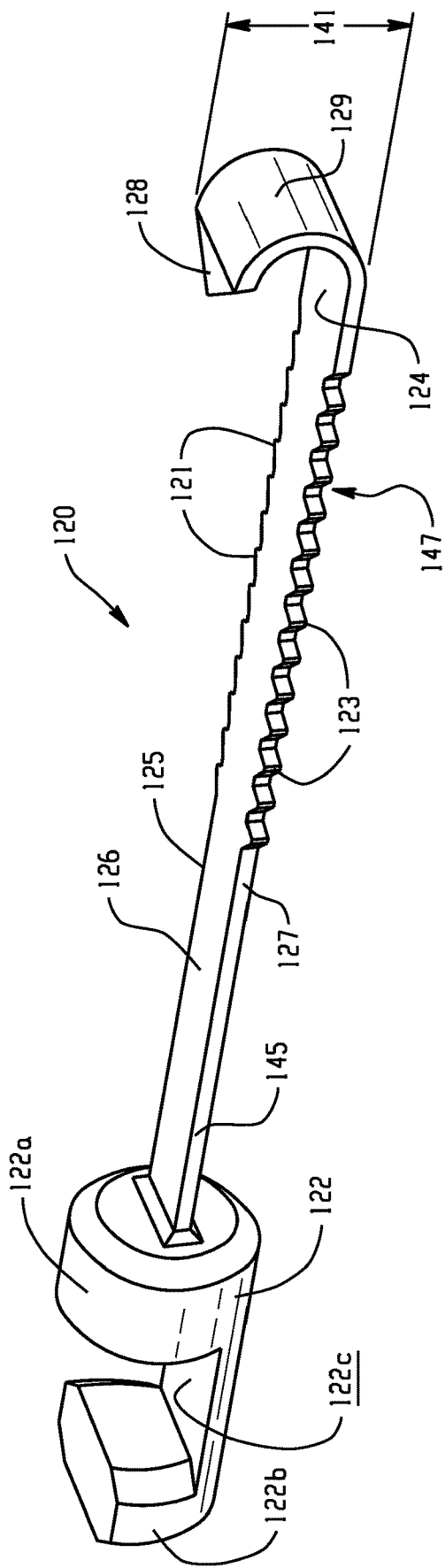
FIG. 5 is a perspective view of an exemplary embodiment of a grasping member according to the present disclosure.
Figure 6:
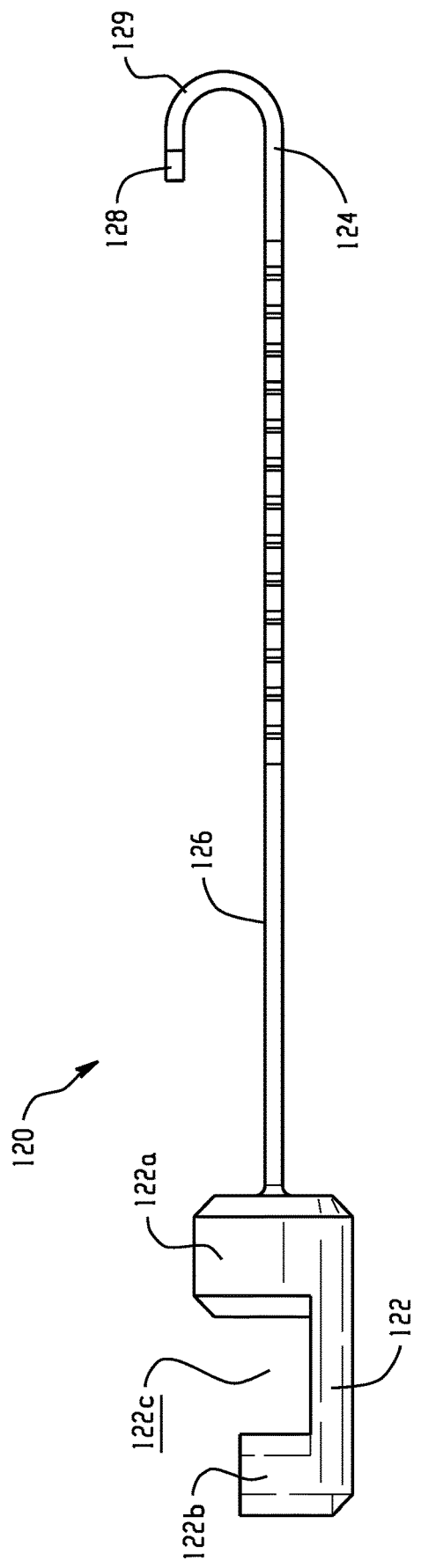
FIG. 6 is a side view of the grasping member of FIG. 5.

FIG. 5 and FIG. 6 show additional features of the grasping member 120 used in the surgical closure device 100. FIG. 5 is a perspective view, and FIG. 6 is a side view.

Referring to both FIG. 5 and FIG. 6 together, at the proximal end 122 of the grasping member, a hollow channel 122c is formed by the base 122a and the lip 122b. Next, the tine 128 of the grasping member 120 is located at the distal end 124. Here, the tine 128 is on an end portion 129 that protrudes away from the main body portion 126, with the tine extending back towards the main body portion 126 so as to form a hook. The end portion 129 and the main body portion 126 meet at a base 124. The base 124 is spaced a fixed distance 141 apart from the tine 128. Put another way, the tine 128 and base 124 do not move relative to one another. In this exemplary embodiment, the end portion 129 of the grasping member 120 forms a hook having a semicircular or U-shaped profile, though it is to be understood that the end portion could have any other suitable shape. The main body portion 126 of the grasping member 120 and the slot 116 in the housing 110 are complementarily shaped so the grasping member 120 cannot rotate within the slot, thereby maintaining the relationship between the receiving portion 118 of the housing 110 and the tine 128 of the grasping member 120.

Now referring only to FIG. 5, the main body portion 126 of the grasping member 120 includes a first side edge 125 and an opposing second side edge 127. While described as "edges," it can be seen that the first and second edges could also be described as faces. In this exemplary embodiment, the first and second side edges 125, 127 of the main body portion 126 of the grasping member 120 are of substantially the same thickness, and the main body portion 126 of the grasping member 120 is planar and has a substantially constant thickness from proximal end 122 to distal end 124. In this exemplary embodiment, each of the first and second side edges 125, 127 includes a smooth region 145 and an engagement region 147. In the engagement region 147, a plurality of protrusions extend outwardly from the main body portion 126. More specifically, the first side edge 125 includes a plurality of protrusions 121, and the second side edge 127 likewise includes a plurality of protrusions 123. The smooth region 145 permits movement of the grasping member in and out of the housing, while the engagement region causes the grasping member to be fixed in a desired position relative to the housing.

In this exemplary embodiment, the protrusions 121, 123 are illustrated as teeth, though it is to be understood that the protrusions 121, 123 could be of any desired size or shape (e.g., teeth, bumps, beads, a combination thereof). Further, while the first and second side edges 125, 127 are both illustrated with the same number and kind of protrusions, it is to be understood that the grasping member could be designed such that: (a) only one of the side edges includes protrusions; (b) the side edges include a different number of protrusions; and/or (c) the side edges include protrusions of different shapes and/or shapes.

Figure 7A:
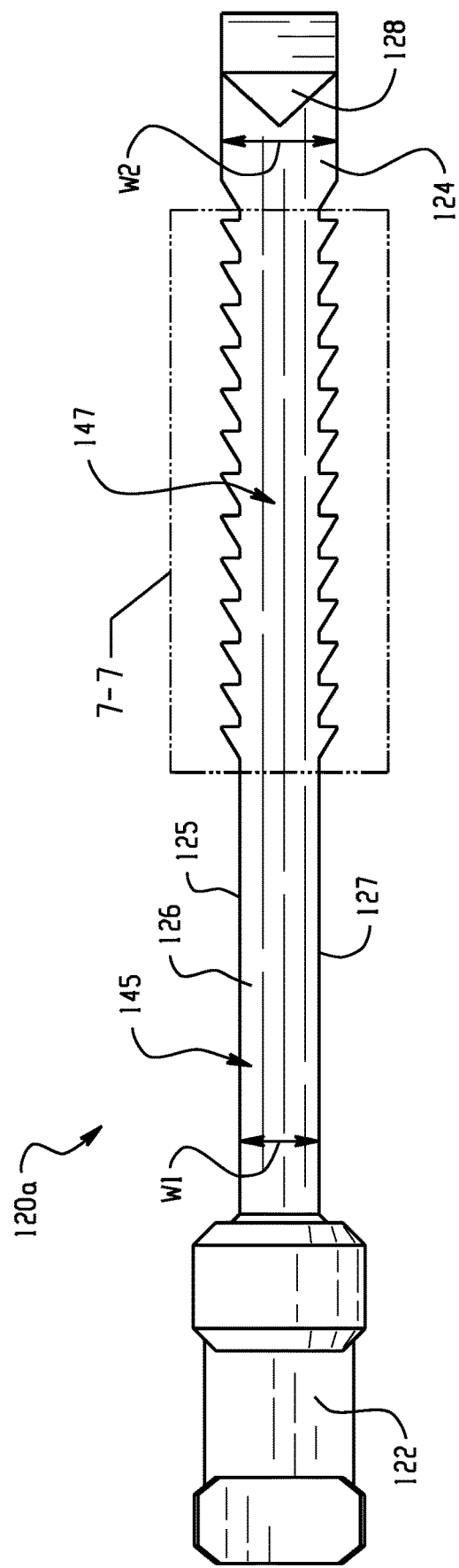
FIG. 7A is a top view of the grasping member of FIG. 5.
Figure 7B:
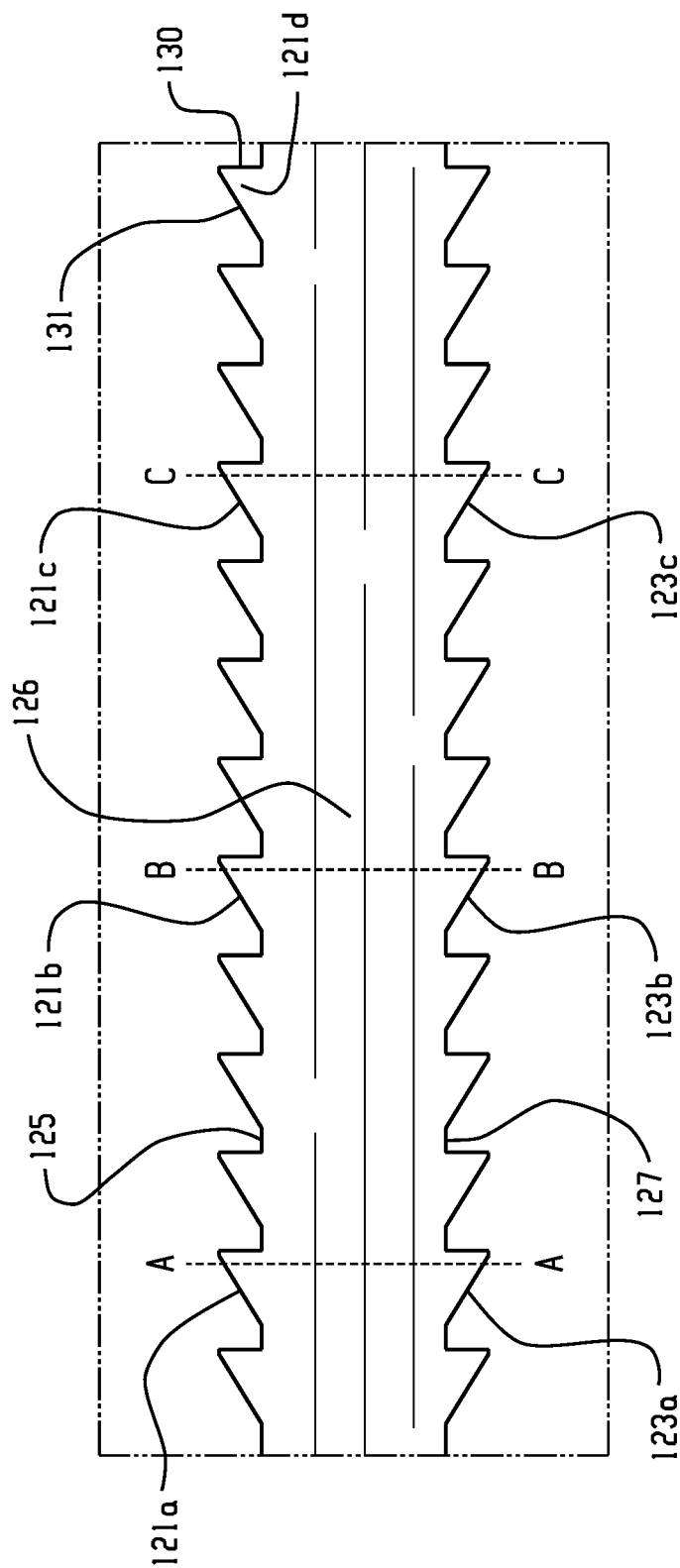
FIG. 7B is a magnified view of section 7-7 of FIG. 7A.
Figure 8A:
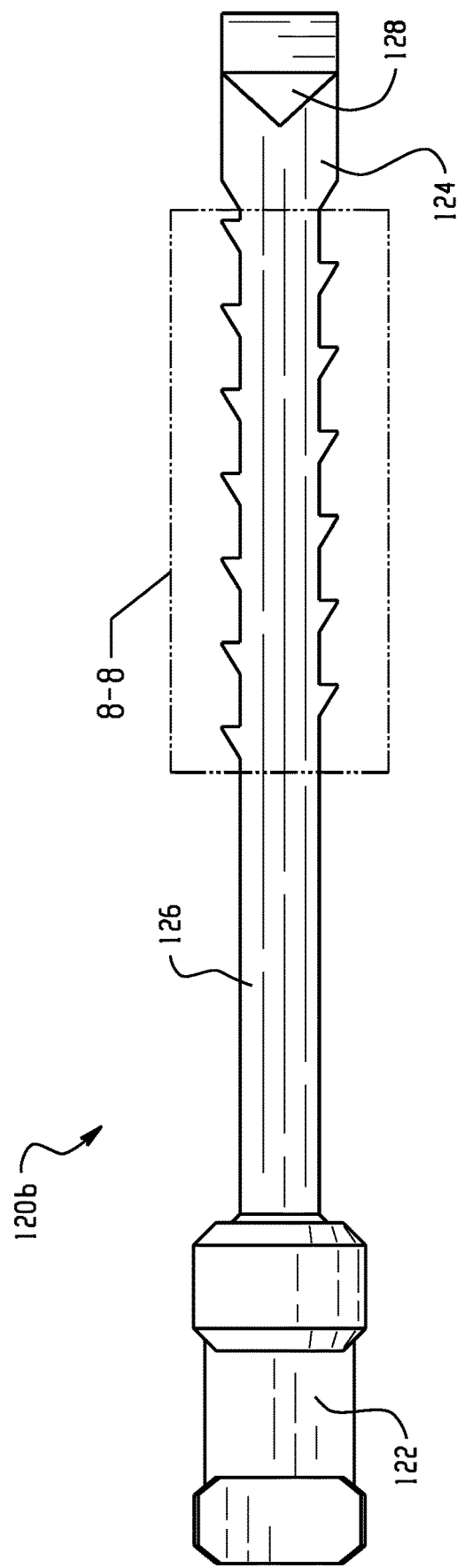
FIG. 8A is a top view of another exemplary embodiment of a grasping member according to the present disclosure.
Figure 8B:
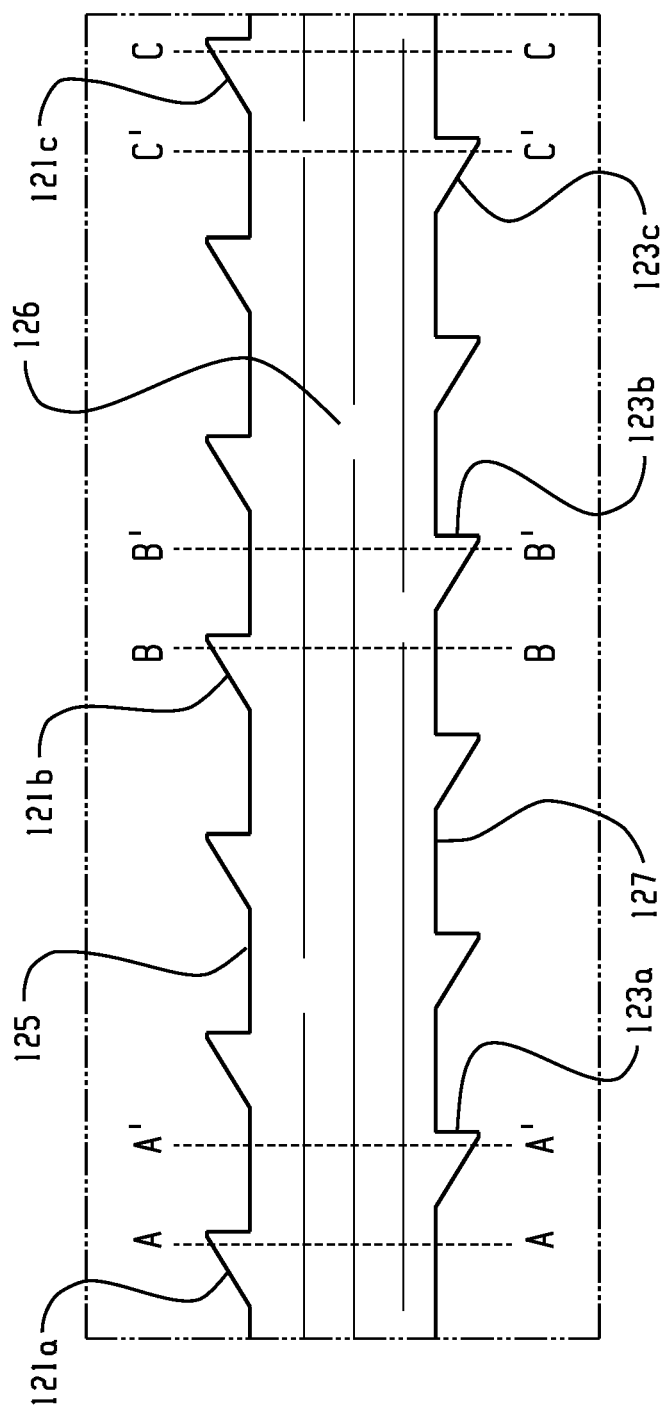
FIG. 8B is a magnified view of section 8-8 of FIG. 8A.

Two different variations of the protrusions are illustrated in FIGS. 7A-7B and FIGS. 8A-8B. FIG. 7A is a top view and FIG. 7B is a magnified view of the first variation. FIG. 8A is a top view and FIG. 8B is a magnified view of the second variation.

Initially, FIG. 7A includes some additional disclosure that applies to all embodiments. The main body portion 126, proximal end 122, and distal end 124 with tine 128 are indicated. The smooth region has a width W1, while the engagement region 147 and the distal end 124 have width W2. The width W1 of the smooth portion is less than the width W2 of the distal end 124 of the grasping member 120. This difference in width will be further discussed later herein.

Continuing, as previously mentioned, the first side edge 125 includes a plurality of protrusions 121 extending outwardly therefrom, and the second side edge 127 also includes a plurality of protrusions 123 extending outwardly therefrom. As seen in FIG. 7A, the protrusions along the first and second side edges 125, 127 of the main body portion 126 of first exemplary grasping member 120a are located in-line with one another. FIG. 7B, which is a magnified view of section 7-7 of FIG. 7A, shows this principle in greater detail.

In this first variation, and referring now to FIG. 7B, each protrusion 121 extending from the first side edge 125 corresponds to a protrusion 123 extending from the second side edge 127 in the same latitudinal level. Put another way, a pair of corresponding protrusions extend parallel to one another from opposing side edges of the main body portion 126 in the same latitudinal level, each latitudinal level having at least one pair of corresponding protrusions. Three pairs of corresponding protrusions are labeled: (i) protrusion 121a extending from the first side edge 125 corresponds to protrusion 123a extending from the second side edge 127, with protrusions 121a, 123a extending parallel to one another at latitudinal level A; (ii) protrusion 121b extending from the first side edge 125 corresponds to protrusion 123b extending from the second side edge 127, with protrusions 121b, 123b extending parallel to one another at latitudinal level B; and (iii) protrusion 121c extending from the first side edge 125 corresponds to protrusion 123c extending from the second side edge 127, with protrusions 121c, 123c extending parallel to one another at latitudinal level C. In this exemplary embodiment, the spacing between latitudinal levels is constant, and the main body portion 126 of the first exemplary grasping member 120a is reflectionally symmetrical.

The teeth-shaped protrusions illustrated herein have a triangular shape. More particularly, as labeled on protrusion 121d in FIG. 7B, each protrusion includes a base portion 130 that extends outwardly from first side edge 125 of the main body portion 126 of the grasping member 120 substantially perpendicular to the first side edge 125. Each protrusion further includes an angled portion 131 that extends from the first side edge 125 and meets the base portion 130 at a point spaced apart from the first side edge 125, with the angled portion 131 being closer to the proximal end 122 of the grasping member 120 than the distal end 124 of the grasping member 120. The base of each protrusion is located closer to the distal end 124 of the grasping member 120 than the proximal end 122.

A second variation is shown with second exemplary grasping member 120b of FIG. 8A and FIG. 8B. As seen in FIG. 8A, the main body portion 126, proximal end 122, and distal end 124 with tine 128 are indicated. Here, the protrusions along the first and second side edges 125, 127 of the main body portion 126 of second exemplary grasping member 120b are staggered or offset relative to one another. FIG. 8B, which is a magnified view of section 8-8 of FIG. 8A, shows this principle in greater detail.

In this second variation, referring now to FIG. 8B, the first side edge 125 includes a plurality of protrusions 121 extending outwardly therefrom, and the second side edge 127 also includes a plurality of protrusions 123 extending outwardly therefrom. In this exemplary embodiment, the protrusions 121 extending from the first side edge 125 and the protrusions 123 extending from the second side edge 127 are arranged in an alternating, staggered manner in different latitudinal levels. Put another way, the location of the protrusions alternates between the two side edges, and there is only one protrusion at a given latitudinal level. As illustrated here, there are protrusions 121a, 121b, and 121c extending from the first side edge 125 at latitudinal levels A, B, and C, respectively, with no protrusions extending from the second side edge 127 at latitudinal levels A, B, or C. Similarly, there are protrusions 123a, 123b, and 123c extending from the second side edge 127 at latitudinal levels A', B', and C', respectively, with no protrusions extending from the first side edge 125 at latitudinal levels A', B', or C'. The distance between latitudinal levels A, B, and C is generally the same as the distance between latitudinal levels A', B', and C'. That is, in this exemplary embodiment, every protrusion extending outwardly from the first side edge 125 is at a different latitudinal level than every protrusion extending outwardly from the second side edge 127. Further, in this exemplary embodiment, the spacing between latitudinal levels is constant, but the main body portion 126 of the second exemplary grasping member 120b is reflectionally asymmetrical.

Figure 9:
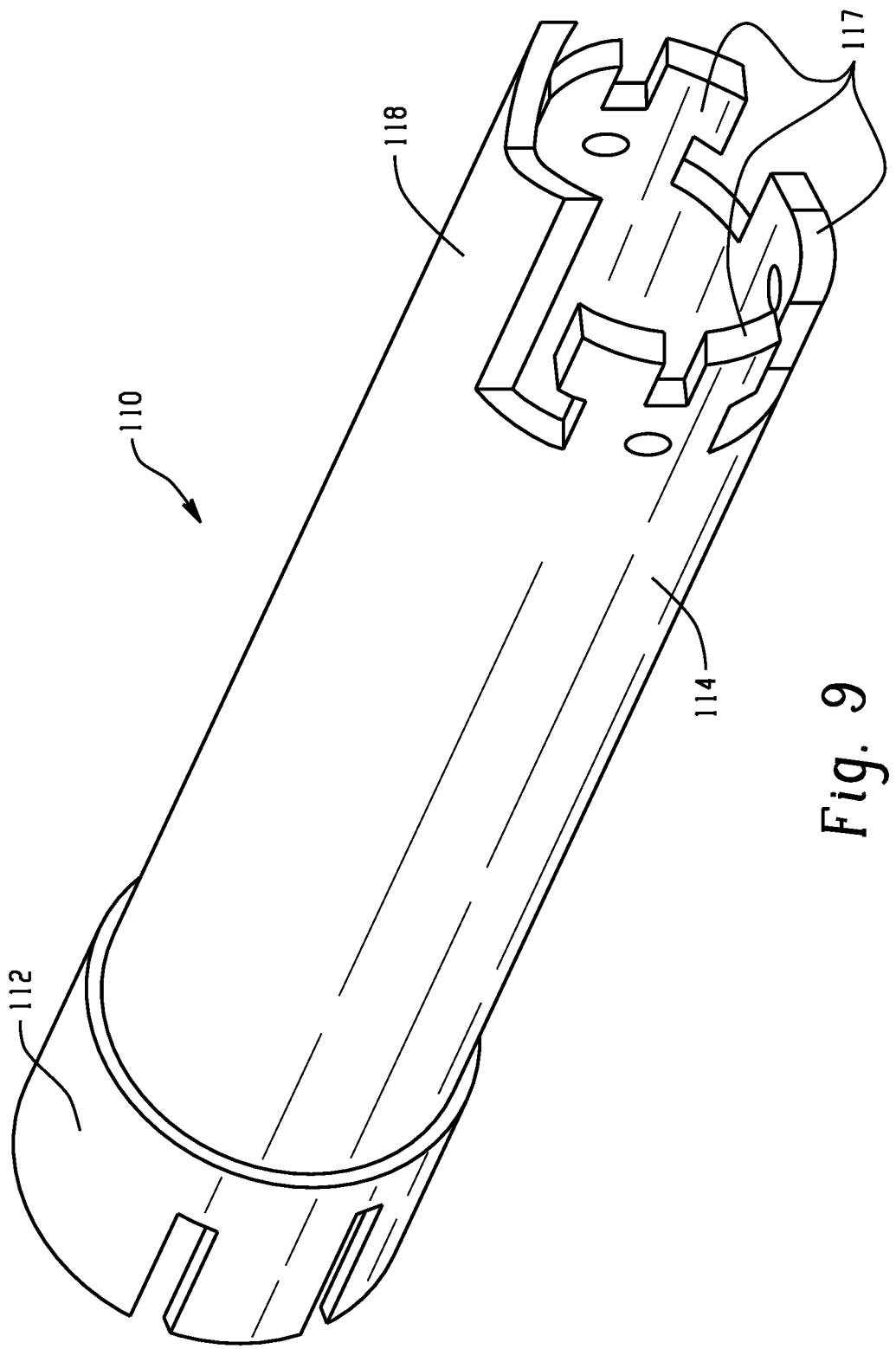
FIG. 9 is a front perspective view of an exemplary embodiment of a housing according to the present disclosure, with the second end hereof in a straight or "open" configuration.
Figure 10:
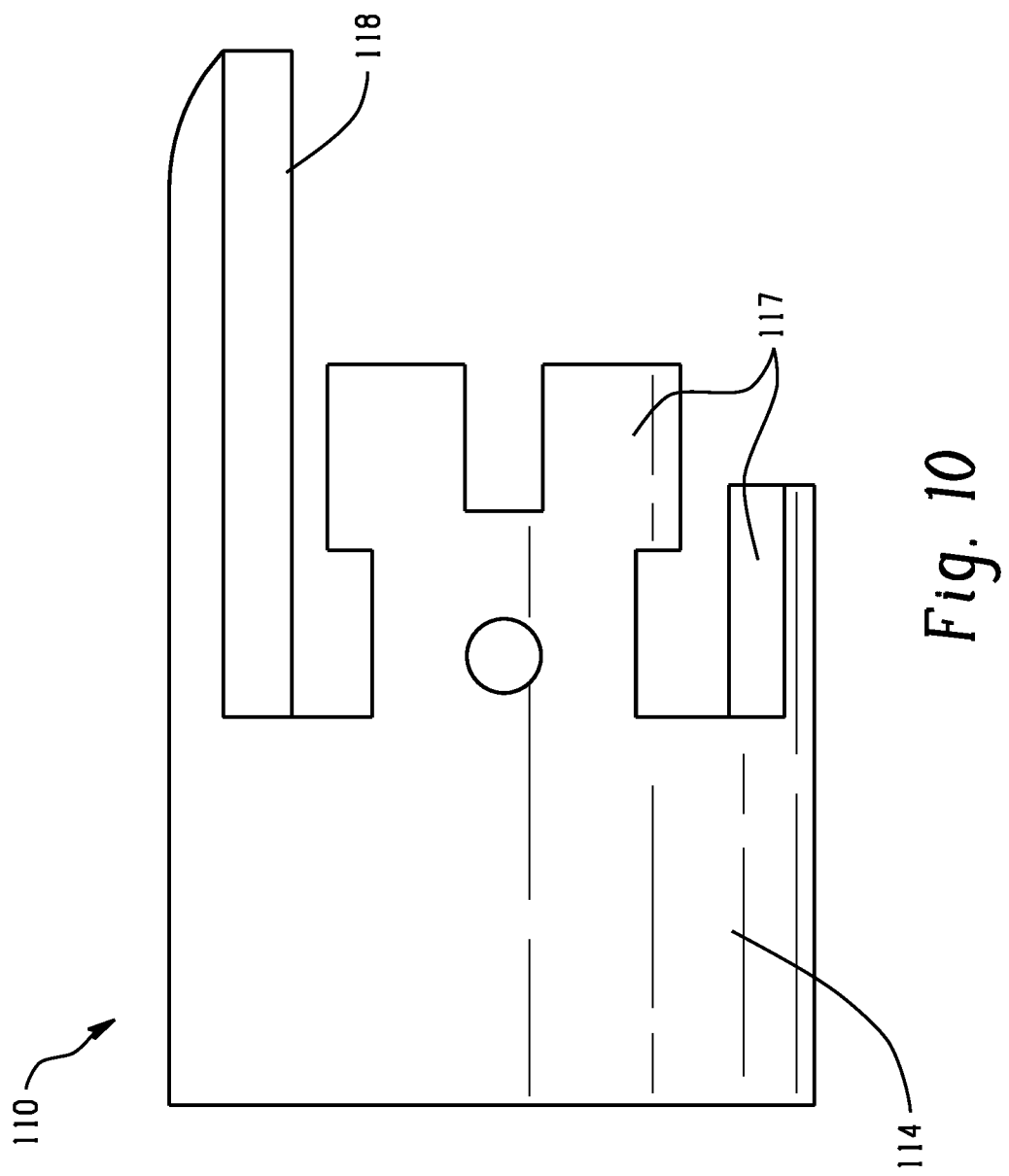
FIG. 10 is a side view of the housing of FIG. 9.
Figure 11:
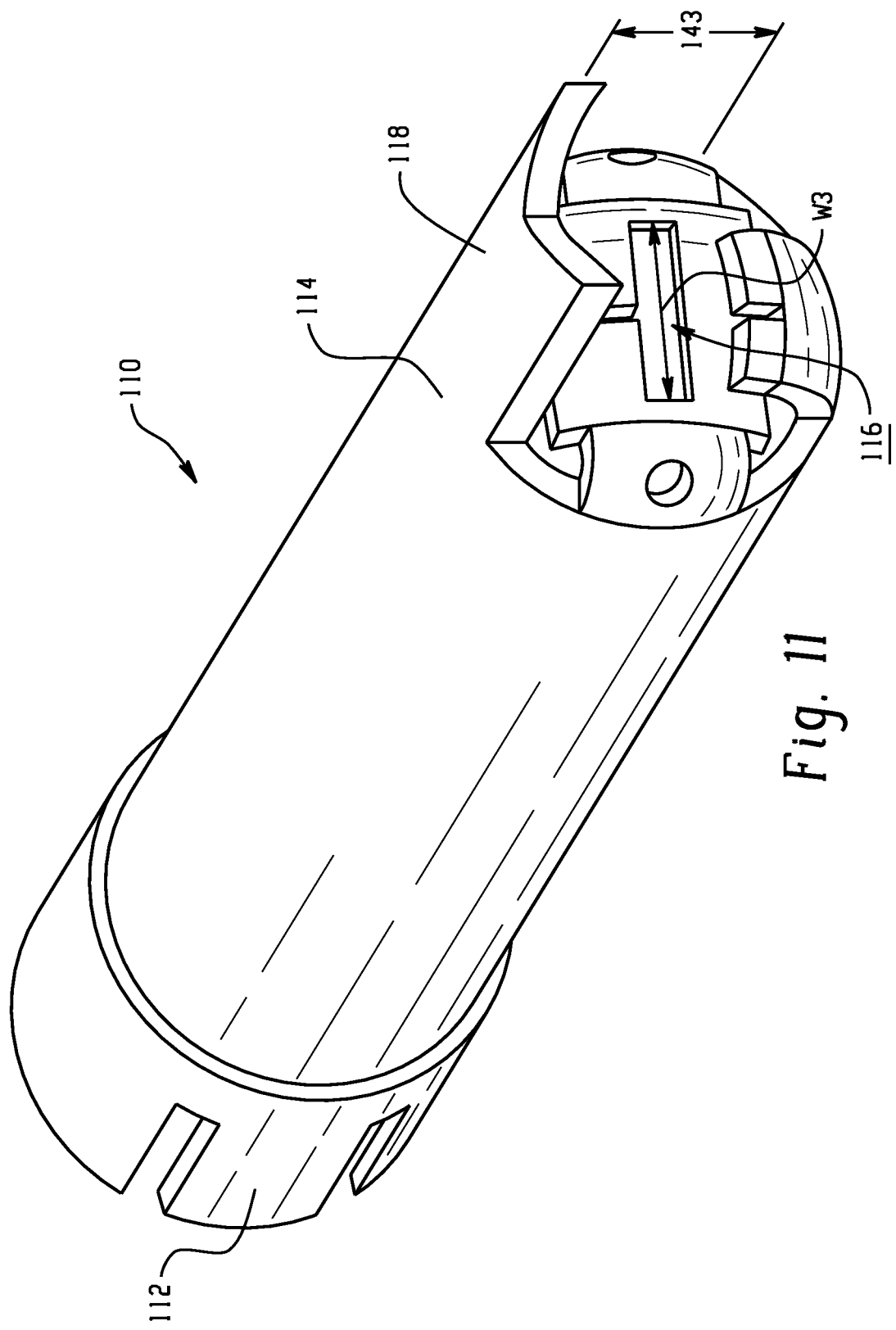
FIG. 11 is a front perspective view of an exemplary embodiment of a housing according to the present disclosure, with the second end hereof in a bent or "closed" configuration.
Figure 12:
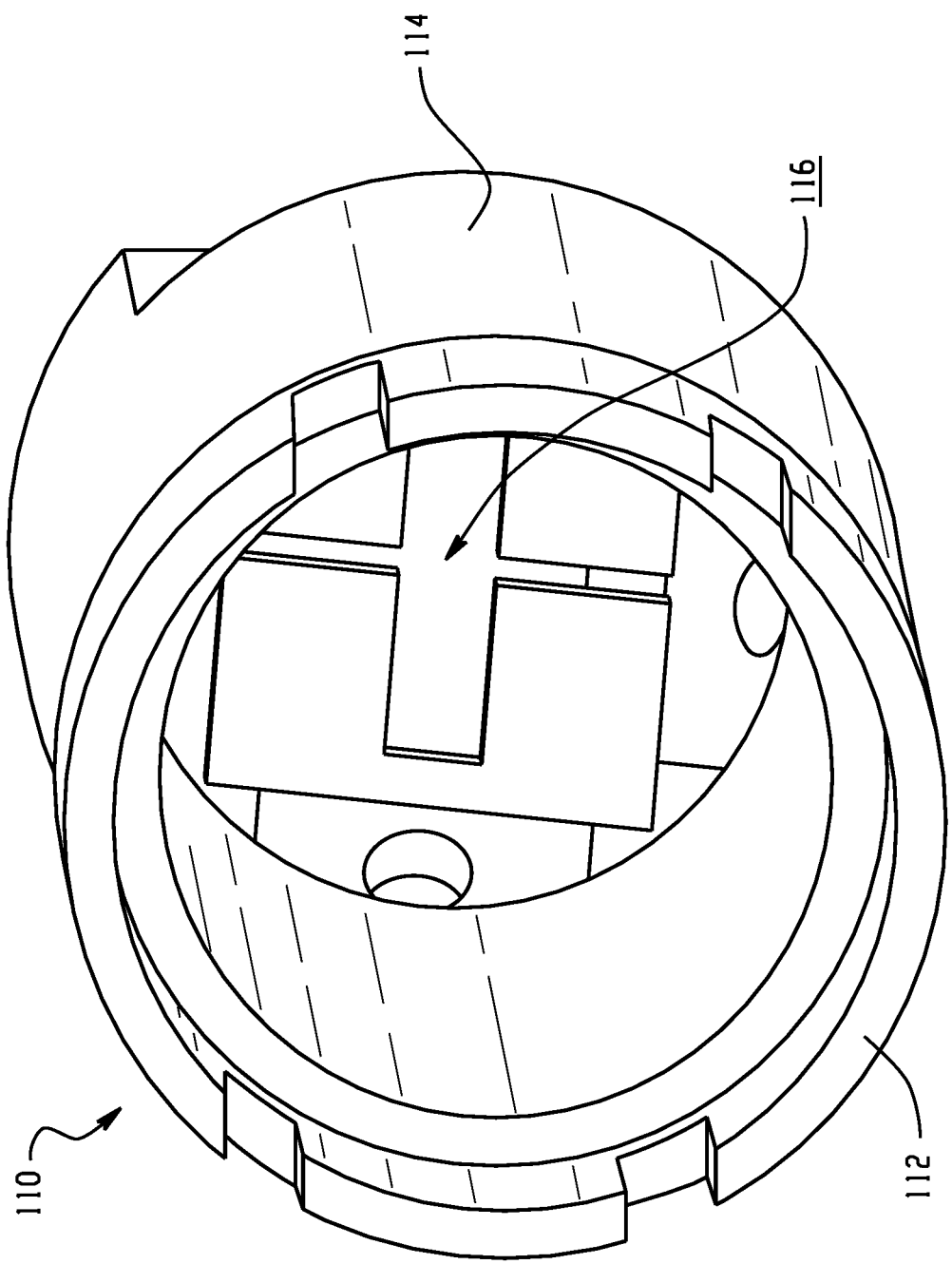
FIG. 12 is a rear perspective view of the housing of FIG. 11.

FIGS. 9-12 show additional views of the housing 110 used in previously-described surgical closure device 100. FIG. 9 is a front perspective view of the housing 100 with the second end 114 thereof in a straight or "open" configuration. FIG. 10 is a side view of the open configuration. FIG. 11 is a front perspective view of the housing 100 with the second end 114 thereof in a bent or "closed" configuration, and FIG. 12 is a rear perspective view of the closed configuration.

As shown in FIG. 9 and FIG. 10, to construct the surgical closure devices of the present disclosure, the second end 114 of the housing 100 can be manufactured in a straight or "open" configuration, so that the grasping member 120 can be placed relative to the housing. In the open configuration, the second end 114 of the housing 110 includes two side elements 117 and a bottom element 115, which are spread out so as to allow the distal end 124 of the grasping member 120 to pass through the second end 114 of the housing 110. The bottom element is 115 opposite the receiving section 118. The slot is not yet formed in this open configuration.

Once the distal end 124 of the grasping member 120 is passed through the second end 114 of the housing 110 (see FIG. 1 and FIG. 2), the elements 115, 117 at the second end 114 of the housing 110 are then bent or closed, as shown in FIG. 11 and FIG. 12, so as to form the slot 116 in the closed configuration. The side elements 117 are first bent closed to form the slot 116. The bottom element 115 is then folded up to secure the side elements.

Referring now to FIG. 11, the slot 116 at the second end 114 of the housing 110 can be seen. The slot 116 can be designed with any desired size or shape, and accommodates the main body portion of the grasping member. The slot and the main body portion are shaped so that the main body portion slides in and out of the housing without unnecessary movement in any direction other than substantially parallel to the axis X-X of the associated endoscope, and in particular so the main body portion cannot rotate within the slot 116.

The slot 116 of housing 110 illustrated in FIG. 11 is rectangularly shaped and is sized just larger than the main body portion of the grasping member. Again, the slot is desirably sized smaller than either of the proximal or distal ends of the grasping member, such that neither is capable of passing therethrough. Here, the slot is marked with width W3. Referring now to FIG. 7A as well, the width W1 of the grasping member is less than width W3. However, the width W2 of the grasping member is greater than width W3. As a result, the slot 116 engages the protrusions 121 illustrated in FIGS. 7A-7B and FIGS. 8A-8B to fix the receiving section 118 and the tine 128 in place relative to each other. Referring again to FIG. 11, in this regard, the slot 116 and the receiving section 118 are spaced apart by distance 143. This distance 143 is substantially equal to the distance 141 in FIG. 5.

As can be further seen in FIG. 11 and FIG. 12, the first end 112 of the housing 110 has a larger cross-sectional area than the second end 114 of the housing 110. This enables the housing to be easily fitted to an endoscope accessory channel (e.g., having a cross-sectional size matching the second end 114 of the housing 110) or other devices with which the surgical closure device can be used by insertion of the other device into the first end 112 of the housing 110. The first end 112 of the housing 110 could alternatively be designed so as to have a smaller cross-sectional area than the second end 114 of the housing, such that the first end 112 of the housing 110 is inserted into the other device The housing and the grasping member can be made of any biocompatible material. This includes materials such as biocompatible polymers, silicone, polyurethane, and metals such as steel or platinum. The material can, in some instances, be dissolvable over a long time period so that the surgical closure device does not need to be removed from the patient in a second operation. The housing and the grasping member should be rigid, so that their relationship to each other is maintained as needed.

Figure 13:
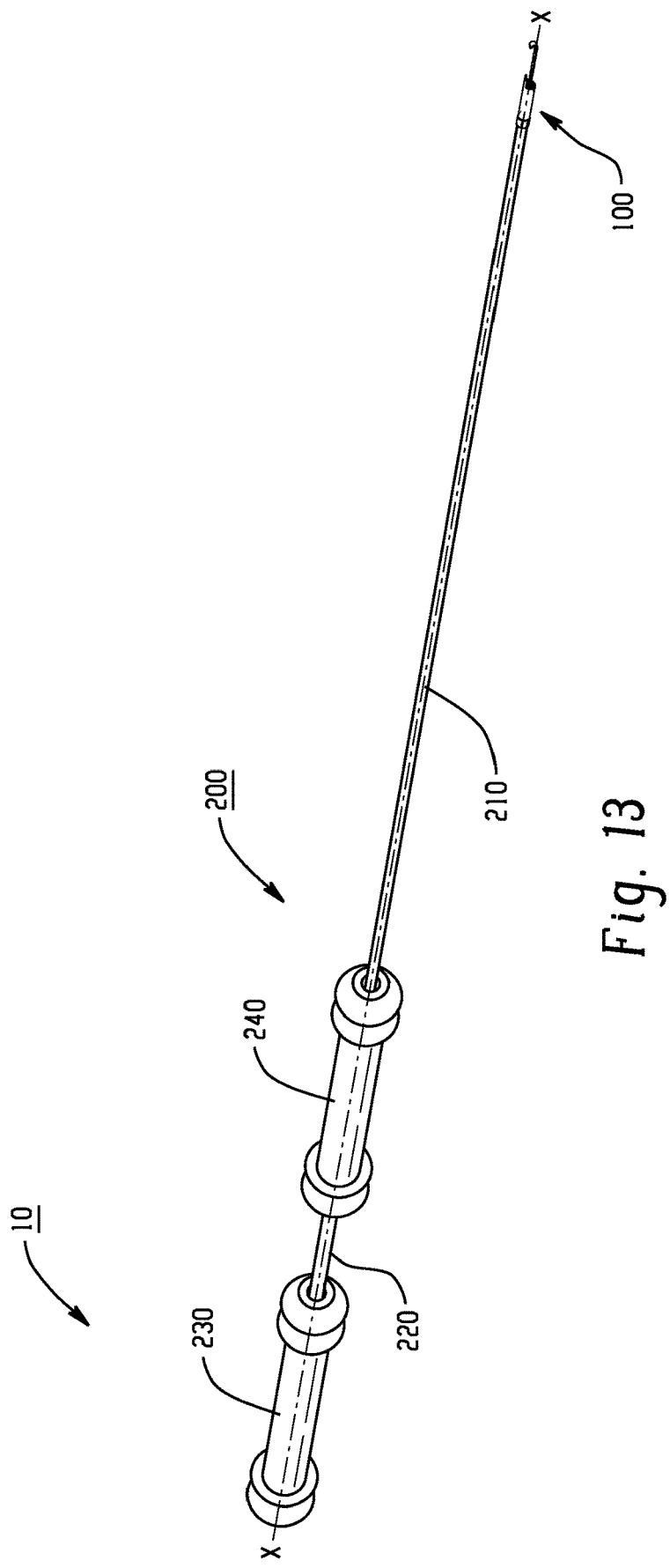
FIG. 13 is a perspective view of an exemplary embodiment of a surgical system according to the present disclosure.
Figure 14:
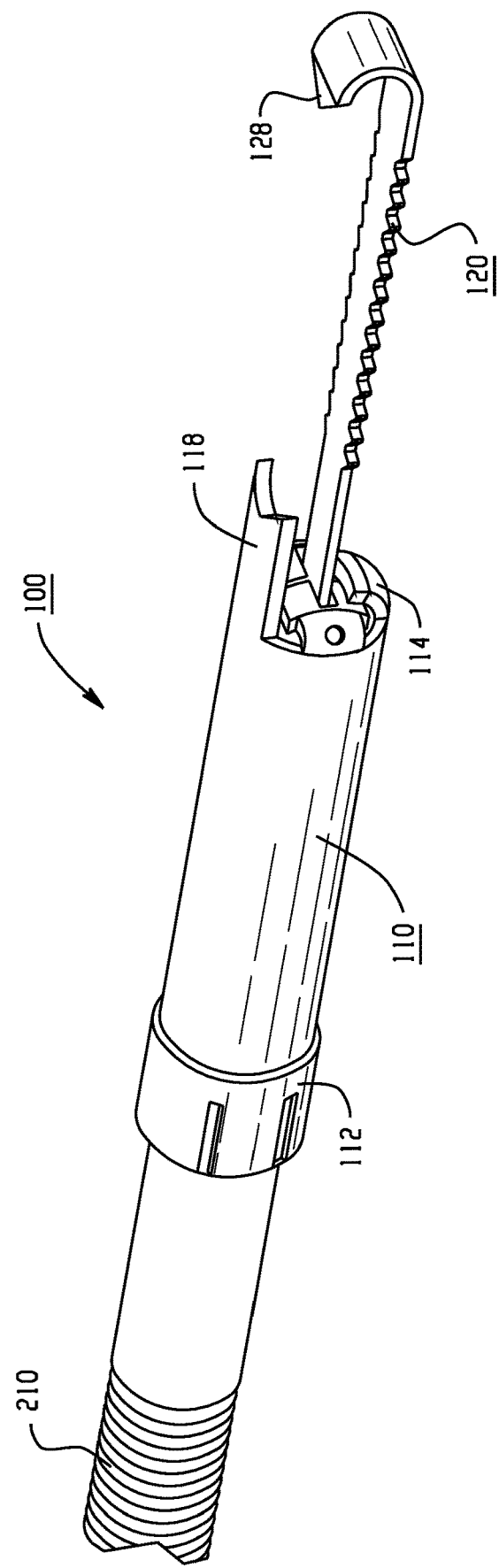
FIG. 14 is a front perspective view of a portion of the surgical system of FIG. 13.
Figure 15:
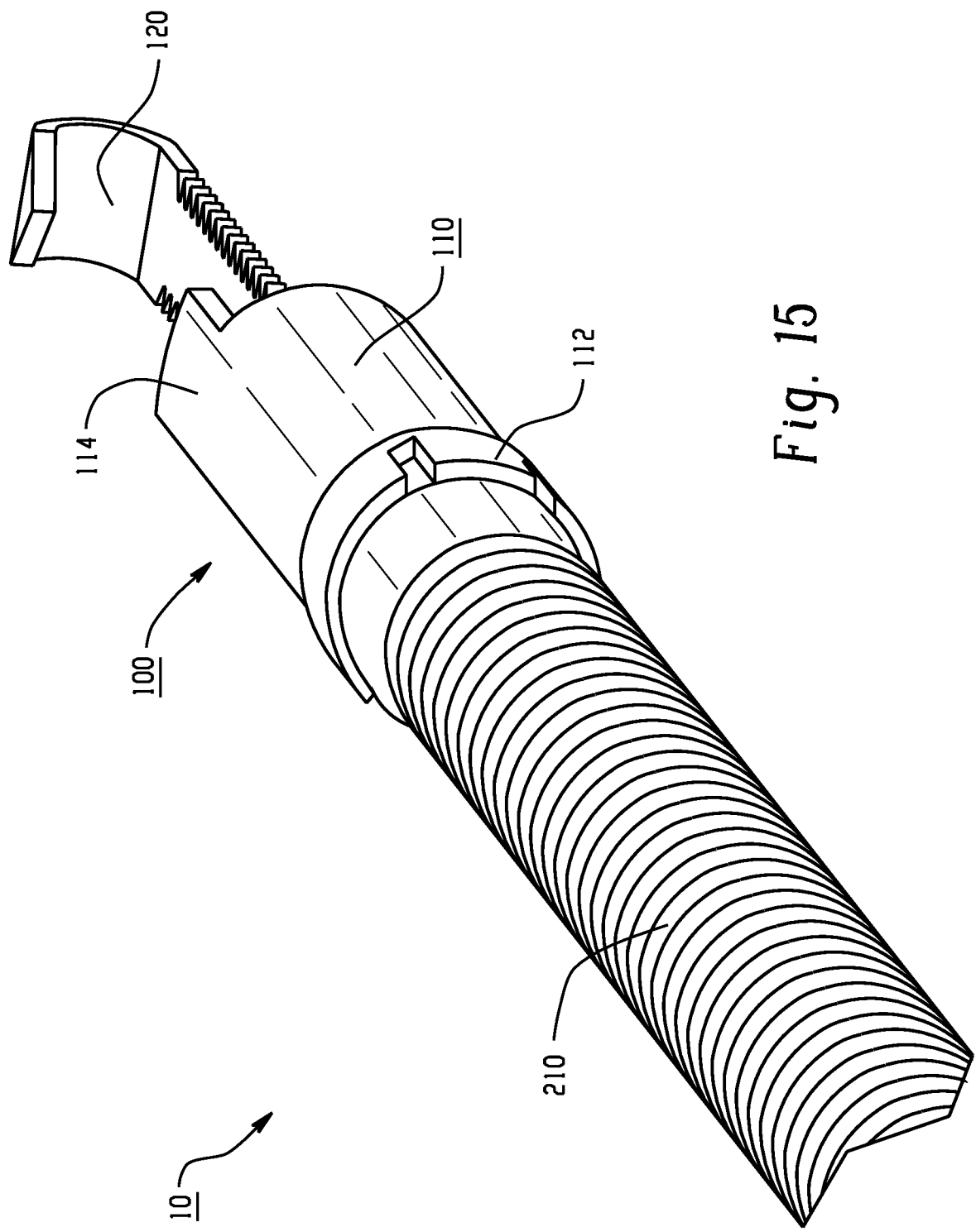
FIG. 15 is a rear perspective view of a portion of the surgical system of FIG. 13.
Figure 16:
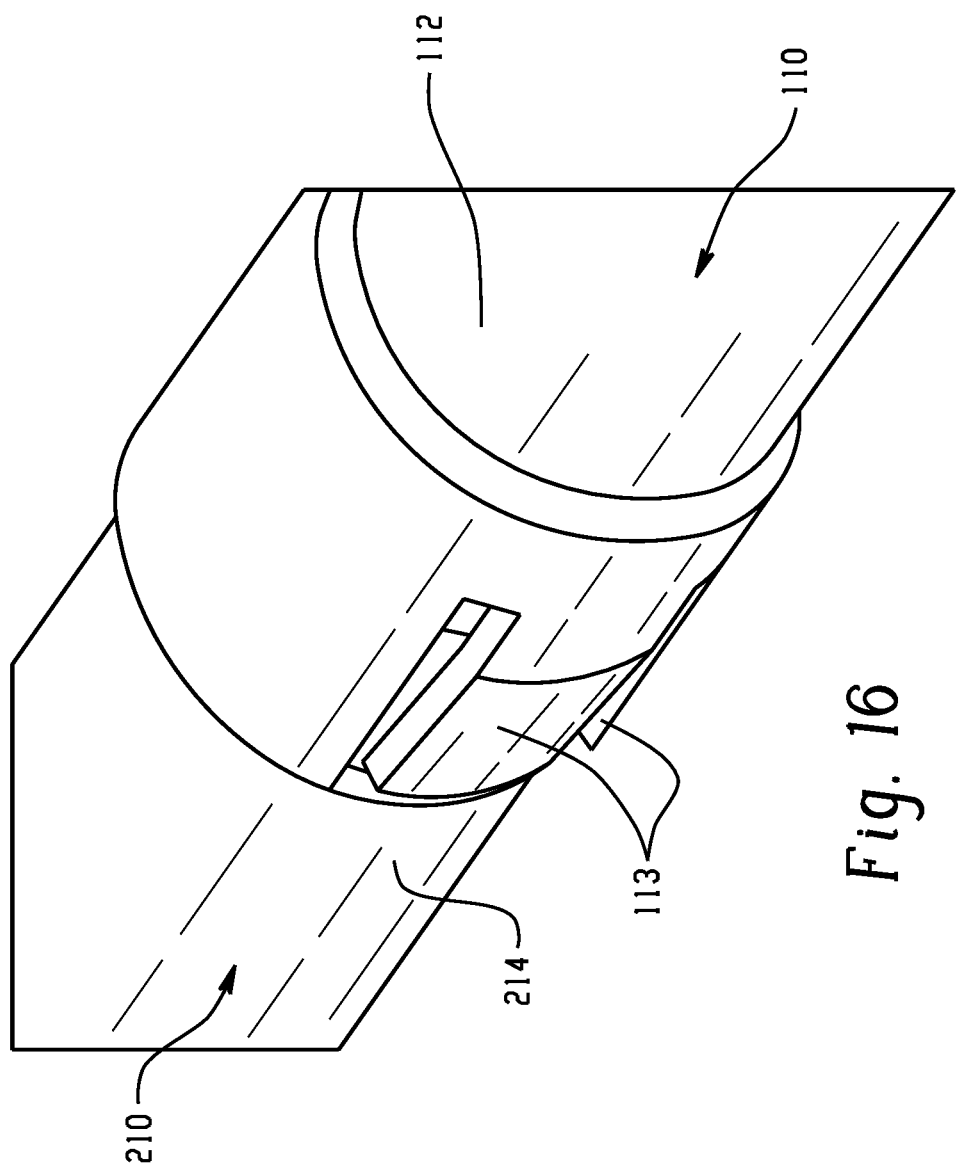
FIG. 16 is another front perspective view of a portion of the surgical system of FIG. 13, particularly showing engagement of the housing and insertion tube thereof.
Figure 17:
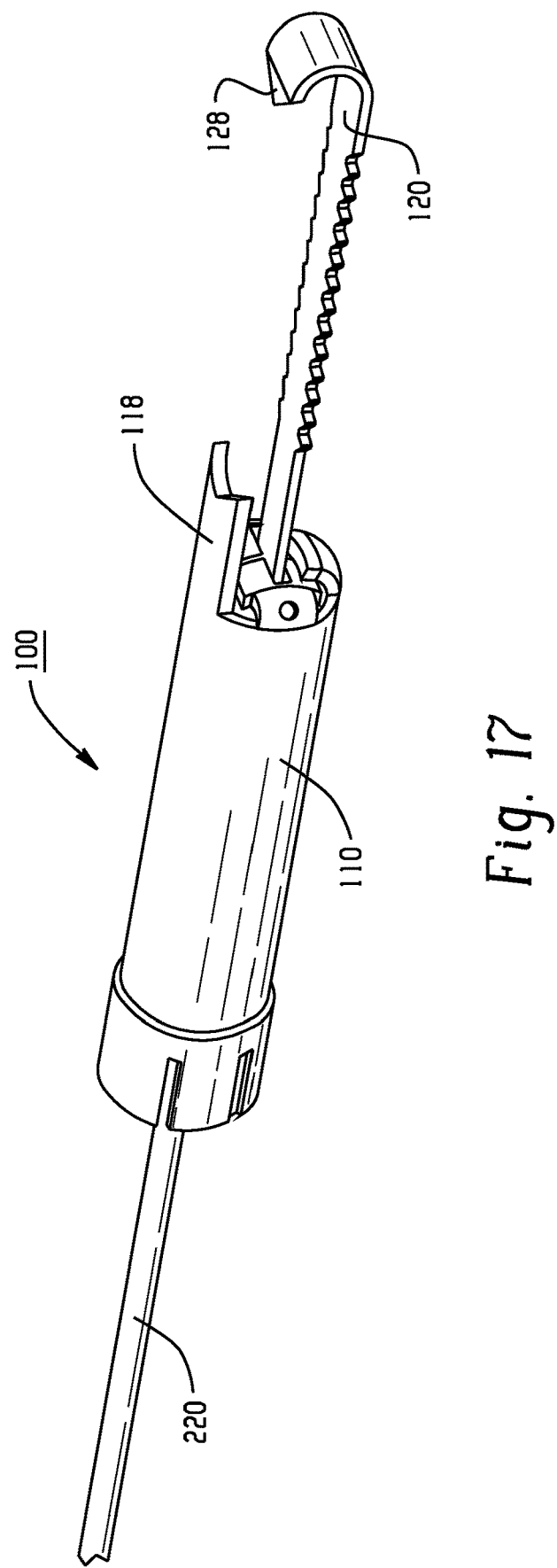
FIG. 17 is another front perspective view of a portion of the surgical system of FIG. 13, with the insertion tube removed to show additional features thereof.
Figure 18:
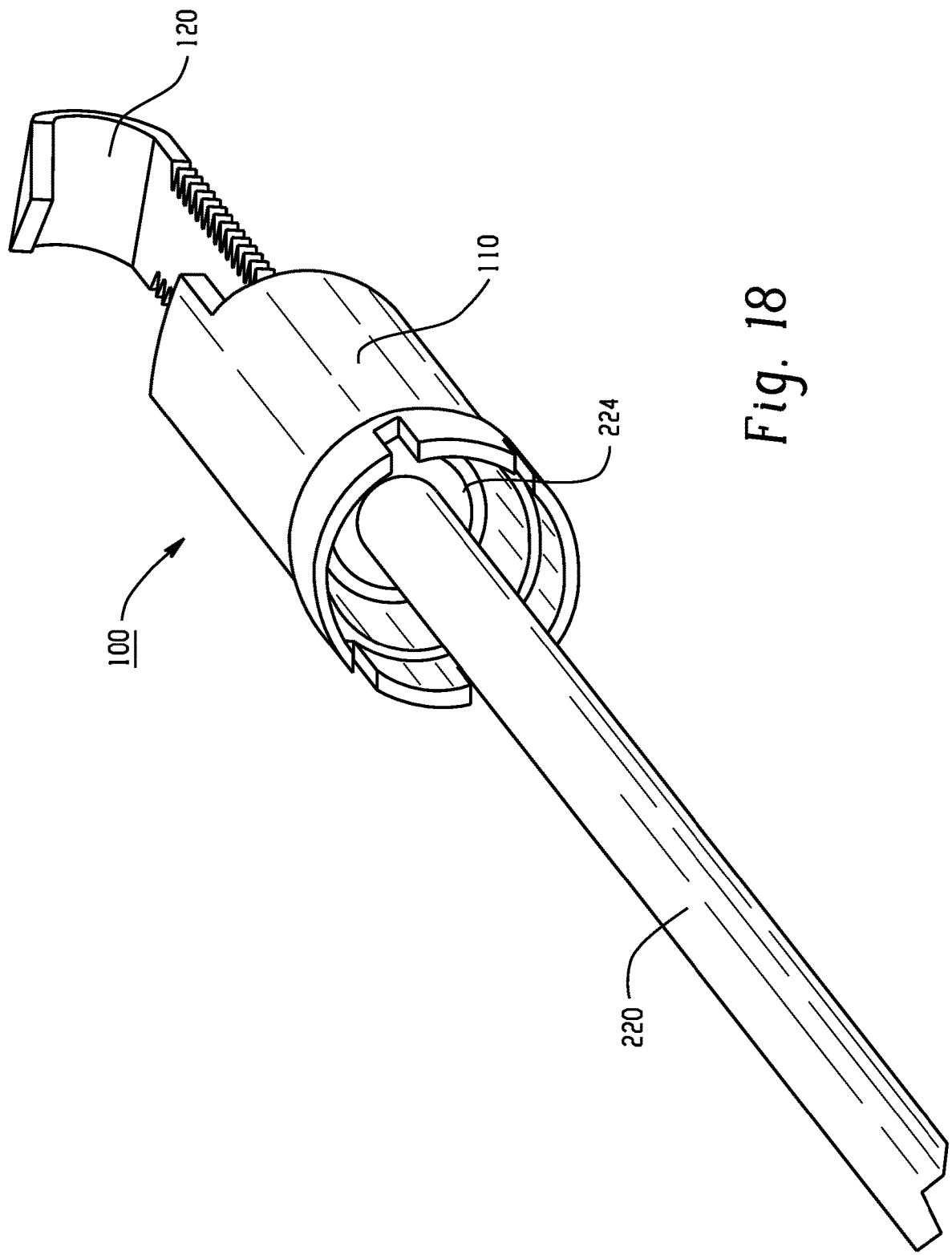
FIG. 18 is a rear perspective view of a portion of the surgical system of FIG. 13, with the insertion tube removed to show additional features thereof.

FIGS. 13-18 show different views of an exemplary embodiment of a surgical system 10 according to the present disclosure. FIG. 13 is a side perspective view of the entire system. FIG. 14 is a magnified view of the surgical closure device 100 at the end of the insertion tube 210. FIG. 15 is a rear perspective view of the surgical closure device 100 with the insertion tube 210. FIG. 16 is a front perspective view of the first end 112 of the housing 110 engaging the insertion tube 210. FIG. 17 is a magnified view of the surgical closure device 100 with the insertion tube removed so the cable 220 is visible. FIG. 18 is a rear perspective view of the surgical closure device 100 with the insertion tube removed so the cable 220 is visible.

Beginning with FIG. 13, the surgical system 10 includes a surgical closure device 100 as previously described. The surgical closure device 100 is coupled to an endoscope 200. More specifically, the surgical closure device 100 engages the insertion tube 210 of the endoscope 200. The endoscope 200 includes first and second handles 230, 240. In this exemplary embodiment, second handle 240 is positioned closer to the surgical closure device 100 than the first handle 230 and engages the insertion tube 210. The first handle 230 engages the cable 220 located within the insertion tube 210. The first handle 230 can be moved relative to the second handle 240, so that the grasping member of the device 100 can be moved relative to the housing of the device 100.

Referring now to FIGS. 14-16, the insertion tube 210 is cooperatively engaged with the first end 112 of the housing 110. Referring first to FIG. 14 and FIG. 15, the grasping member 120 extends out from the second end 114. The receiving section 118 and the tine 128 are in an open position. Note that the grasping member 120 cannot rotate relative to the housing 110, so that the receiving section 118 and the tine 128 remain lined up with each other. FIG. 16 is a magnified view showing how the first end 112 engages the insertion tube 210. The first end 112 of the housing 110 includes flanges 113 that are bent inward toward one another, thereby engaging and grasping the insertion tube 210 along the distal end 214 thereof.

As seen in FIG. 17 and FIG. 18, the cable 220 extends into the housing 110 to engage the grasping member 120. The end 224 of the cable is visible in FIG. 18. As previously described, the end 224 of the cable 220 is cooperatively engaged with the proximal end of the grasping member 120. The cable 220 is sized so as to be able to slide into the first end 112 of the housing 110.

Referring back to FIG. 13, the movement of the first handle 230 relative to the second handle 240 enables movement of the grasping member relative to the housing. In use, the first handle 230 and the second handle 240 begin in a position close to each other, so the receiving section 118 and the tine 128 are separated from each other (i.e. open position). Upon grasping the two sides of the tissue tear that is desired to be closed, the first handle 230 is moved backwards away from the second handle 240, joining the receiving section 118 and the tine 128 together (i.e. closed position). This also permits the cable end 224 to be separated from the proximal end 122 of the grasping member (see FIG. 2). The second handle 240 is then moved backwards towards the first handle 230. The tissue tear now holds the device in place, and the flanges 113 at the first end 112 of the housing 110 (see FIG. 16) release the housing and the grasping member from the insertion tube 210, permitting the endoscopic tool to be removed from the body while leaving the device behind to close the tissue tear.

Referring to FIG. 13 and FIG. 17 simultaneously, the tine 128 is moved towards the receiving section 118 when the first handle 230 is moved away from the second handle 240. This causes the cable 220 to pull on the grasping member. Some back-and-forth motion is afforded by the smooth region 145 of the grasping member (see FIG. 7A). It is contemplated that the surgical closure device is used to close a tear. The two opposite flaps of skin on either side of the tear are joined together between the tine 128 and the receiving section 118.

The design of the present surgical closure device, which operates with the grasping member moving in parallel relative to the endoscope cable, provides forward-and-backward opening, compared to the right-and-left opening of other such closure devices In addition, no penetration of the gastrointestinal wall lumen is required to close the tear, compared to other devices.

The present disclosure has been described with reference to preferred embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A surgical closure device, comprising:
   a housing comprising a longitudinal axis, a first end, a second end opposite the first end, a slot at the second end of the housing, and a receiving portion at the second end of the housing and spaced apart from the slot; and
   a grasping member comprising a proximal end, a distal end opposite the proximal end, and a tine at the distal end of the grasping member, the grasping member passing through the slot in the housing and configured for movement relative to the housing such that the tine can engage the receiving portion of the housing;
   wherein the grasping member further comprises a main body portion that passes through the slot in the housing, the main body portion of the grasping member includes a first side edge and a second side edge opposite the first side edge, at least one of the first and second side edges having a plurality of protrusions extending outwardly therefrom, wherein the protrusions engage the housing to retain the tine of the grasping member in a fixed relationship relative to the receiving portion of the housing.

2. The surgical closure device of claim 1, wherein the grasping member is configured for bi-directional movement toward the housing and away from the housing along a direction parallel to the longitudinal axis of the housing.

3. The surgical closure device of claim 1, wherein the receiving portion of the housing and the tine of the grasping member are complementarily shaped.

4. The surgical closure device of claim 1, wherein each of the plurality of protrusions includes a base portion and an angled portion, the base portion extending outwardly from the first side edge substantially perpendicular thereto, and the angled portion extending outwardly from the first side edge and meeting the base portion at a point spaced apart from the first side edge, with the angled portion being closer to the proximal end of the grasping member than the distal end of the grasping member.

5. The surgical closure device of claim 1, wherein each of the first and second side edges has a plurality of protrusions extending outwardly therefrom.

6. The surgical closure device of claim 5, wherein every protrusion extending outwardly from the first side edge corresponds to a respective protrusion extending outwardly from the second side edge to define a pair of corresponding protrusions that are positioned in a same latitudinal level and parallel to one another.

7. The surgical closure device of claim 5, wherein every protrusion extending outwardly from the first side edge is at a different latitudinal level than every protrusion extending outwardly from the second side edge.

8. The surgical closure device of claim 1, wherein the tine of the grasping member is located on an end portion of the grasping member, the end portion protruding outwardly from the main body portion of the grasping member.

9. The surgical closure device of claim 8, wherein the end portion of the grasping member includes a base that is spaced a fixed distance apart from the tine.

10. The surgical closure device of claim 1, wherein the proximal end of the grasping member comprises:
a base that engages the main body portion, the base being wider than the slot in the housing; and
a lip extending away from the main body portion.

11. A surgical system, comprising:
an endoscope including an insertion tube having a cable disposed therein; and
a surgical closure device adapted to be delivered by the endoscope, the surgical closure device including:
a housing comprising a longitudinal axis, a first end, a second end opposite the first end, a slot at the second end of the housing, and a receiving portion at the second end of the housing and spaced apart from the slot; and
a grasping member comprising a proximal end, a distal end opposite the proximal end, and a tine at the distal end of the grasping member, the grasping member passing through the slot in the housing and configured for movement relative to the housing;
wherein the grasping member further comprises a main body portion that passes through the slot in the housing, the main body portion of the grasping member includes a first side edge and a second side edge opposite the first side edge, at least one of the first and second side edges having a plurality of protrusions extending outwardly therefrom, wherein the protrusions engage the housing to retain the tine of the grasping member in a fixed relationship relative to the receiving portion of the housing;
wherein the insertion tube of the endoscope is cooperatively engaged with the first end of the housing; and
wherein the cable of the endoscope is cooperatively engaged with and adapted to move the grasping member relative to the housing such that the tine can engage the receiving portion of the housing.

12. The surgical system of claim 11, wherein an end of the cable is shaped complementary to the proximal end of the grasping member such that the proximal end of the grasping member cooperatively engages with the end of the cable.

13. The surgical system of claim 11, wherein the endoscope further comprises a first handle and a second handle, wherein the first handle is adapted for movement relative to the second handle and cooperatively engages with the cable, and wherein the second handle engages the insertion tube, such that the first handle moves the grasping member relative to the housing of the surgical closure device.

14. The surgical system of claim 11, wherein the receiving portion of the housing and the tine of the grasping member are complementarily shaped.

15. The surgical system of claim 11, wherein the the first and second side edges of the main body portion each have a plurality of protrusions extending outwardly therefrom that can engage the slot of the housing.

16. The surgical system of claim 11, wherein the proximal end of the grasping member comprises:
a base that engages the main body portion, the base being wider than the slot in the housing; and
a lip extending away from the main body portion, the lip engaging the cable of the endoscope.

17. A method of endoscopically closing a tear in a tissue, the method comprising:
passing a surgical closure device through an endoscope to the tear, the surgical closure device including:
a housing comprising a longitudinal axis, a first end, a second end opposite the first end, a slot at the second end of the housing, and a receiving portion at the second end of the housing and spaced apart from the slot; and
a grasping member comprising a proximal end, a distal end opposite the proximal end, and a tine at the distal end of the grasping member, the grasping member passing through the slot in the housing and configured for movement relative to the housing;
wherein the grasping member further comprises a main body portion that passes through the slot in the housing, the main body portion of the grasping member includes a first side edge and a second side edge opposite the first side edge, at least one of the first and second side edges having a plurality of protrusions extending outwardly therefrom, wherein the protrusions engage the housing to retain the tine of the grasping member in a fixed relationship relative to the receiving portion of the housing;
engaging a portion of tissue on one side of the tear using the tine of the grasping member;
positioning the receiving portion of the housing on another side of the tear; and
moving the tine of the grasping member toward the receiving portion of the housing to position the tine of the grasping member and the receiving portion of the housing in a relatively closed relationship, thereby closing the tear in the tissue.

* * * * *